US012636248B2

(12) United States Patent
Ramanathan et al.

(10) Patent No.: US 12,636,248 B2
(45) Date of Patent: May 26, 2026

(54) NUTRACEUTICALS FORMULATION WITH AN ENHANCED ORGANOLEPTIC PROPERTIES USED FOR SKIN CARE

(71) Applicant: DiaBliss Consumer Products Pvt Ltd, Chennai (IN)

(72) Inventors: Vr. Ramanathan, Chennai (IN); Siva Vallabhaneni, Chennai (IN); V. Rajalakshmi, Chennai (IN)

(73) Assignee: DiaBliss Consumer Products Pvt Ltd, Chennai (IN)

( * ) Notice: Subject to any disclaimer, the term of this patent is extended or adjusted under 35 U.S.C. 154(b) by 326 days.

(21) Appl. No.: 18/261,332

(22) PCT Filed: Jan. 17, 2022

(86) PCT No.: PCT/IN2022/050034
§ 371 (c)(1),
(2) Date: Jul. 13, 2023

(87) PCT Pub. No.: WO2022/153337
PCT Pub. Date: Jul. 21, 2022

(65) Prior Publication Data
US 2024/0074964 A1 Mar. 7, 2024

(30) Foreign Application Priority Data
Jan. 16, 2021 (IN) .............................. 202141002108

(51) Int. Cl.
| A61K 36/00 | (2006.01) |
| A61K 8/9789 | (2017.01) |
| A61K 36/185 | (2006.01) |
| A61Q 3/00 | (2006.01) |
| A61Q 19/08 | (2006.01) |

(52) U.S. Cl.
CPC .......... A61K 8/9789 (2017.08); A61K 36/185 (2013.01); A61Q 3/00 (2013.01); A61Q 19/08 (2013.01); *A61K 2800/5922* (2013.01)

(58) Field of Classification Search
CPC ...................................................... A61K 36/54
See application file for complete search history.

(56) References Cited

U.S. PATENT DOCUMENTS

| 2007/0122492 | A1* | 5/2007 | Behr | .................... | A61K 8/9789 |
| | | | | | 424/754 |
| 2016/0153968 | A1* | 6/2016 | Wadhwa | .............. | C12N 15/113 |
| | | | | | 435/320.1 |

FOREIGN PATENT DOCUMENTS

| IN | 750/CHE/2008 | 7/2008 |
| KR | 101015909 B1 | 2/2011 |
| KR | 20130012042 A | 1/2013 |
| WO | 200653415 A1 | 5/2006 |

OTHER PUBLICATIONS

WO, International Search Report; PCT/IN2022/050034, May 4, 2022, 12 pages.

* cited by examiner

*Primary Examiner* — Qiuwen Mi
(74) *Attorney, Agent, or Firm* — Kevin J Fournier Intellectual Property Legal Services Ltd.; Kevin J Fournier

(57) ABSTRACT

Nutraceutical formulations, which could be used for wholistic skin care and treatment purposes, with enhanced organoleptic properties have elements of biological origin more particularly a herbal formulation(s).

10 Claims, 6 Drawing Sheets

Figure 1:
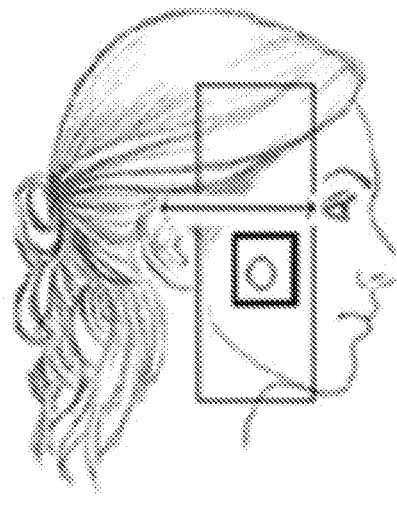

NUTRACEUTICALS FORMULATION WITH AN ENHANCED ORGANOLEPTIC PROPERTIES USED FOR SKIN CARE

CROSS-REFERENCE TO RELATED APPLICATIONS

The present invention is filed under 35 U.S.C. § 371 as the U.S. national phase of International Patent Application No. PCT/IN2022/050034, filed Jan. 17, 2022, which designated the United States and which claims the benefit of Indian Patent Application number 202141002108, filed Jan. 16, 2021, which is hereby incorporated in its entirety including all tables, figures, and claims.

FIELD OF THE INVENTION

The subject matter described herein, in general, relates to a nutraceuticals formulation, which could be used for Skin care purposes, with an enhanced organoleptic properties. Said formulation have elements of biological origin more particularly a herbal formulation(s).

BACKGROUND OF THE INVENTION

Sunlight is a major cause of the skin changes we think of as aging—changes such as wrinkles, dryness, and age spots. As people age skin changes in many ways. For example, one tends to sweat less, leading to increased dryness. As skin ages, it also becomes thinner and loses fat, so it looks less plump and smooth. Underlying structures—veins and bones in particular—become more prominent. Skin can take longer to heal when injured.

Every day the cells of the outer layer of skin die off, shed, and regenerate. When young, skin cells turn over quickly, but that turnover rate begins to slow with age, beginning as early as twenties. As a result, skin loses its luster and begins to look dull. Aging caused by the genes we inherit is called intrinsic (internal) aging. The other type of aging is known as extrinsic (external) aging and is caused by environmental factors, such as exposure to the sun's rays.

Skin ageing is mainly characterized by the following:

Decrease in thickness, firmness & elasticity of skin which results in wrinkles.

Reduction in antioxidant capacities.

Formation of spider veins and dark circles under the eyes.

The epidermis, dermis and subcutaneous tissues are the top, middle and bottom layers of the skin respectively. The top layer shows the wrinkles, age spots, deep lines, and depressions. The skin dermis contains macromolecules, polysaccharides, glycosaminoglycans (GAGs), fibrous protein (collagens, elastin), salts and water which together are known as the extra cellular matrix, responsible for tissue cohesion.

The subcutaneous tissues contain fatty deposits. Another part of the skin is the sebaceous glands that produce sebum which lubricates the skin and keeps it soft and smooth. All three skin layers contribute to the aging process. As a person gets older, less sebum is produced, and this makes the epidermis drier. Dry skin is more prone to wrinkling.

Signs of ageing includes facial wrinkles, pigmentation, fine lines, crow's feet and Nasolabial folds. Ageing also impacts texture and elasticity of the skin.

Pigmentation errors like uneven skin tone, blemishes, blotchiness and spots also results in varied reflectance of light from the skin surface and results in dullness of the skin.

It is also known that skin hydration, skin texture and pigmentation concerns can impact the skin glow.

Wrinkles

Over time, the sun's ultraviolet (UV) light damages the fibers in the skin called elastin. The breakdown of these fibers causes the skin to lose its ability to snap back after stretching. As a result, wrinkles form. Most wrinkles associated with aging appear on the parts of the body where sun exposure is greatest. These sites are the face, neck, the backs of the hands, and the tops of the forearms. Wrinkles come in two categories: fine surface lines and deep furrows related to muscular contraction. Gravity also is at work, pulling at the skin and causing it to sag, most noticeably on the face, neck, and upper arms.

Cigarette smoking also contributes to wrinkles. People who smoke tend to have more wrinkles than nonsmokers of the same age, complexion, and history of sun exposure. The reason for this difference is not clear. It may be because smoking also plays a role in damaging elastin. Facial wrinkling increases with the number of cigarettes and number of years a person has smoked.

Dry Skin and Itching

Many older individuals suffer from dry skin, particularly on their lower legs, elbows, and forearms. The skin feels rough and scaly and often is accompanied by a distressing, intense itchiness. Low humidity—caused by overheating during the winter and air conditioning during the summer—contributes to dryness and itching. The loss of sweat and oil glands as you age also may worsen dry skin. Anything that further dries your skin—such as overuse of soaps, antiperspirants, perfumes, or hot baths—will make the problem worse. Dehydration, sun exposure, smoking, and stress also may cause dry skin.

Dry skin and itching can affect sleep, cause irritability, or be a symptom of a disease. For example, diabetes and kidney disease can cause itching.

One thing that we cannot change is the natural aging process. It plays a key role. With time, we all get visible lines on our face. It is natural for our face to lose some of its youthful fullness. We notice our skin becoming thinner and drier. Our genes largely control when these changes occur. The medical term for this type of aging is "intrinsic aging."

We can influence another type of aging that affects our skin. This relates to our environment and lifestyle choices which can cause our skin to age prematurely. The medical term for this type of aging is "extrinsic aging." By taking some preventive actions, we can slow the effects that this type of aging has on our skin.

Ways to Reduce Premature Skin Aging

There are many ways to reduce premature ageing. These methods normally are temporary and are summarized below:

1. Protecting of skin from the sun every day. One can protect skin by seeking shade, covering up with sun-protective clothing—such as a lightweight and long-sleeved shirt, pants, a wide-brimmed hat, and sunglasses with UV protection—and using sunscreen that is broad-spectrum, and water-resistant.

2. Avoiding smoking as smoking greatly speeds up how quickly skin ages. It causes wrinkles and a dull, sallow complexion.

3. Avoiding repetitive facial expressions. When you make a facial expression, you contract the underlying muscles. If you repeatedly contract the same muscles for many years, these lines become permanent. Wearing sunglasses can help reduce lines caused by squinting.

4. Eating a healthy, well-balanced diet. Findings from studies suggest that eating plenty of fresh fruits and vegetables may help prevent damage that leads to premature skin aging. Findings from research studies also suggest that a diet containing lots of sugar or other refined carbohydrates can accelerate aging.

5. Drinking less alcohol as alcohol dehydrates the skin, and in time, damages the skin.

6. Exercise regimen—findings from studies suggest that moderate exercise can improve circulation and boost the immune system. This, in turn, may give the skin a more-youthful appearance.

7. Cleansing of skin gently as scrubbing skin clean can irritate skin which in turn accelerates skin aging.

8. Application of facial moisturizer keeps skin hydrated, giving it a more youthful appearance.

9. Avoid use of skin care products that sting or burn as it means skin is irritated. Irritating skin can make it look older.

Several interventions described above work on protective mechanisms and use of topical solutions that basically address skin health superficially. Further many surgical interventions that have become popular involve surgical/plastic surgery procedures and injecting serums, Botox treatments to provide foundational base of fats and saccharides to the inner layers of the skin. These interventions only achieve superficial and temporary results.

The present invention pertains to use of herbal extracts from various herbs and spices that are consumed in a water-soluble form that modifies the intrinsic properties of the skin by addressing the fundamental mechanisms that cause skin conditions such as wrinkles, blemishes, pigmentation, and other disorders such as eczema and psoriasis. These conditions may arise from variety of factors including normal ageing process, exposure to sun light, hormonal imbalances and inflammation.

While wrinkles are formed as a natural part of the ageing process, which tend to be accentuated by UV exposure, many hormonal changes also tend to accelerated skin wrinkles. Estrogen stimulates collagen, one of the proteins responsible for the elasticity and smoothness of the skin. With less estrogen circulating in the bloodstream, women are more likely to develop fine lines, wrinkles, and loose skin. In men, lower testosterone levels can cause a similar effect on the skin. Many of the commonly consumed foods, herbs, and spices contain phytoestrogens and phytoprogestins that act as agonists and antagonists in vivo.

The biggest risk factors for general hyperpigmentation are sun exposure and inflammation, as both situations can increase melanin production. Hormonal influences are the main cause of a particular kind of hyperpigmentation known as melasma or chloasma. It's particularly common among women and is thought to occur when the female hormones estrogen and progesterone stimulate the overproduction of melanin when skin is exposed to the sun. Many natural materials including various herbs have shown to be effective to address hyperpigmentation.

Psoriasis is a skin disorder that causes skin cells to multiply up to 10 times faster than normal. This makes the skin build up into bumpy red patches covered with white scales. Psoriasis is thought to be an immune system problem. Topical ointments, light therapy, and medications can offer temporary relief. By addressing immunity related issues at the root cause level such as nutraceuticals that deliver antioxidants the herbal formulations can address these issues holistically.

While the exact cause of eczema is unknown, researchers do know that people who develop eczema do so because of a combination of genes and environmental triggers. When an irritant or an allergen from outside or inside the body "switches on" the immune system, it produces inflammation. It is this inflammation that causes the symptoms common to most types of eczema. So in many cases herbal nutraceuticals tend to address the causative environmental factors that may cause inflammation such as allergens and tend to address root causes of eczema Wound & Burn Healing and Scarring:

Wound healing is a complex biological process that consists of hemostasis, inflammation, proliferation, and remodeling. Large numbers of cell types—including neutrophils, macrophages, lymphocytes, keratinocytes, fibroblasts, and endothelial cells—are involved in this process. Multiple factors can cause impaired wound healing by affecting one or more phases of the process and are categorized into local and systemic factors.

Burn injuries are caused by fires or flames, hot liquids or steam, contact with a hot object or agent like grease or tar, chemicals, or electricity. First-, Second- or Third-degree burns are classified based on the layers of skin that are impacted. Treatments can range from simple at home treatments to ointments & bandages to surgery and grafting to address more severe third-degree burns.

Herbal extract ingredients contain anti-bacterial, anti-fungal, anti-viral, anti-microbial, anti-inflammatory and anti-oxidant properties. These ingredients can also assist in treating skin wounds and burns by preventing infection, speeding up the healing process and reducing bruising and scarring. They promote faster healthy skin rejuvenation and hydration while helping the immune system fight bacteria. Active ingredients in turmeric (*Curcuma longa*), long pepper (*Curcuma longa*), guava leaves (*Psidium guajava*), basil (*Ocimum basilicum*) and chia seeds (*Salvia hispanica*) are known to possess the desired properties to enhance wound & burn healing, skin rejuvenation, increase in wound breaking strength while protecting the skin layers from infections as an adjuvant therapy.

Skin Dryness and Itchiness

As we age, sweat and oil glands don't produce as much moisture. Fat and collagen, substances that gives skin its elasticity, decrease and Skin becomes thinner. Skin that's too dry may crack open and bleed. These cracks expose the body to germs that can cause infections. Some illnesses, including diabetes and kidney disease, can cause dry, itchy skin. As a result, the cumulative effect of these changes results in dry skin on our legs, elbows, arms or other parts of the body. The medical term for dry skin is xerosis. Allergies (dermatitis), irritants and skin conditions like eczema can also make skin dry and itchy.

Moisturizers are the mainstay of treatment for most types of dry skin. They smooth and soften dry skin to help prevent cracking and work to recreate your natural skin barrier. Moisturizing products come in ointments, creams, lotions and oils.

The ingredients used in the current invention and the accompanying examples show significant impact of consuming the herbal waters on various parameters pertaining to skin health and particularly skin hydration, glow, elasticity characteristics and described in detail in Example 1. These ingredients therefore will assist in lowering skin dryness and itchiness.

Vitiligo

Vitiligo occurs when immune cells destroy the cells that make brown pigment called melanocytes. This destruction is thought to be due to an autoimmune problem. An autoimmune disorder occurs when the body's immune system, which normally protects the body from infection, attacks and destroys healthy body tissue instead. The exact cause of vitiligo is unknown.

There is no cure for vitiligo but several treatment options are available. Therapies include steroids and the combination of ultraviolet light in combination with creams. Due to the higher risks of skin cancer, phototherapy is used only if primary treatments are ineffective.

The ingredients found in current formulation are known to possess immunity boosting and anti-inflammatory properties. The current formulation has shown to address other autoimmune based disorders such as eczema and psoriasis and therefore could also address Vitiligo as an adjunctive therapy.

Skin & Hair Conditions in Chemotherapy

Cancer treatment can affect a person's skin, hair, and nails. The reason chemotherapy can cause hair loss is that it targets all rapidly dividing cells—healthy cells as well as cancer cells. Hair follicles, the structures in the skin from which hair grows, include some of the fastest-growing cells in the body. Other conditions that occur as a result of chemo therapy include, rashes, dry & itchy skin, nail conditions that cause nails to lift, break, or develop light or dark streaks or grooves.

Acne, also known as acne vulgaris, is a long-term skin condition that occurs when dead skin cells and oil from the skin clog hair follicles. Typical features of the condition include blackheads or whiteheads, pimples, oily skin, and possible scarring which mostly impacts teenage population. It primarily affects skin with a relatively high number of oil glands, including the face, upper part of the chest, and back. Treatments for acne are available, including lifestyle changes, medications, and medical procedures. Treatments applied directly to the affected skin, such as azelaic acid, benzoyl peroxide, and salicylic acid, are commonly used. Antibiotics and retinoids are available in formulations that are applied to the skin and taken by mouth for the treatment of acne. However, resistance to antibiotics may develop as a result of antibiotic therapy. Herbal ingredients with anti-inflammatory, anti-bacterial, immunity enhancing and exfoliating properties have been shown the be effective in treatment of Acne.

By consuming nutraceuticals from herbs and spices, the required ingredients for skin health are supplied to various layers of the skin to provide and inside out solution to skin health versus topical solutions which tend to be external and temporary in nature. Further, Acanthosis nigricans (AN), is a skin condition that causes small patches of skin, often near the knuckles, to darken, thicken, and become velvety to the touch.

Splits may occur in the fingernails, resulting in thin layers of the nails peeling back. There are many different causes of peeling or splitting nails. This condition is called Onychoschizia. Nails consist of layers of a protective fibrous protein called keratin that also occurs in skin and hair. Keratin makes the nails strong, but various underlying health conditions can cause thin layers of the nail to peel away.

By consuming nutraceuticals from herbs and spices, the required ingredients for skin health are supplied to various layers of the skin to provide and inside out solution to skin health versus topical solutions which tend to be external and temporary in nature.

SUMMARY OF THE INVENTION

In the last three decades, a lot of concerted efforts have been channeled into researching into local plants with therapeutic values to address various health and wellness issues. The beneficial effects of some of these plants, herbs or spices have been validated and others disproved.

It is an object of the present invention to provide for a water based herbal formulation that addresses skin care management, skin related disorders and diseases among human subjects. The product formulation is prepared using the embodiments described in the Indian Patent application no: 202041041780 and the same is incorporated herewith by reference.

A herbal formulation for skin care management comprising essentially of a therapeutically effective amount of *Daucus carota, Amaranthus gangeticus* L., *Eclipta prostrata, Phyllanthus emblica, Curcuma longa, Piper longum, Psidium guajava, Ocimum basilicum, Salvia hispanica, Juglans regia, Linum usitatissimum, Prunus dulcis, Piper nigrum, Murraya koenigii, Glycyrrhiza glabra, Cinnamomum Zeylanicum Blume, Cuminum cyminum, Trigonella foenum-graecum, Beta vulgaris, Punica granatum.*

The aforesaid herbal formulation broadly comprises of the herbal constituents in the range of *Daucus carota* 0%-2.0%, *Amaranthus gangeticus* L 0-0.5%, *Eclipta prostrata* 0%-1.5%, *Phyllanthus emblica* 1.5%-10.5%, *Curcuma longa* 1.0%-11.0%, *Piper longum* 0.5%-6.5%, *Psidium guajava* 7.0%-30%, *Ocimum basilicum* 5.0%-28.0%, *Salvia hispanica* 0.5%-6.5%, *Juglans regia* 2.0%-27.5%, *Linum usitatissimum* 0.75%-6.5%, *Prunus dulcis* 1.75%-15.0%, *Piper nigrum* 1%-10%, *Murraya koenigii* 1.25%-7.5%, *Glycyrrhiza glabra* 1.0%-11.0%, *Cinnamomum zeylanicum* Blume 2%-13.5%, *Cuminum cyminum* 0.25%-6.0%, *Trigonella foenum-graecum* 3.5%-22.0%, *Beta vulgaris* 0%-1.5%, *Punica granatum* 0%-2.85%.

The herbal formulation of the present invention could be manufactured using parts of the plants used for preparing the extracts are *Daucus carota* seeds, *Amaranthus gangeticus* L leaves, *Eclipta prostrata* leaves & stem, *Phyllanthus emblica* fruit, *Curcuma longa* root, *Piper longum* fruit, *Psidium guajava* leaves, *Ocimum basilicum* leaves, *Salvia hispanica* Seeds, *Juglans regia* Seed, *Linum usitatissimum* Seeds, *Prunus dulcis* Seeds, *Piper nigrum* flower, *Murraya koenigii* leaves, *Glycyrrhiza glabra* root, *Cinnamomum zeylanicum* Blume bark, *Cuminum cyminum* seeds, *Trigonella foenum-graecum* seeds, *Beta vulgaris* taproot, *Punica granatum* seeds & fruit.

As another embodiment the herbal formulation of the present invention comprises of the herbal constituents present in the range of *Daucus carota* 1.0%, *Amaranthus gangeticus* l 0.1%, *Eclipta prostrata* 0.70%, *Phyllanthus emblica* 6.0%, *Curcuma longa* 6.0%, *Piper longum* 2.4%, *Psidium guajava* 18.0%, *Ocimum basilicum* 17.7%, *Salvia hispanica* 3.6%, *Juglans regia* 6.0%, *Linum usitatissimum* 3.0%, *Prunus dulcis* 6.0%, *Piper nigrum* 4.0%, *Murraya koenigii* 2.8%, *Glycyrrhiza glabra* 5.8%, *Cinnamomum zeylanicum* Blume 5.5%, *Cuminum cyminum* 3.0%, *Trigonella foenum-graecum* 7.0%, *Beta vulgaris* 0.4%, *Punica granatum* 0.9%.

BRIEF DESCRIPTION OF ACCOMPANYING DRAWINGS

FIG. 1: Cutometer Measurement Areas

Figure 2:
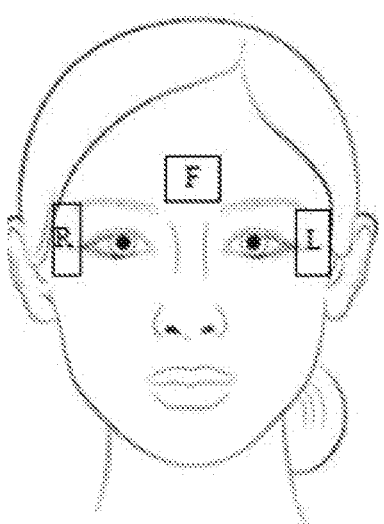

FIG. 2: Antera Measurement Areas

Figure 3:
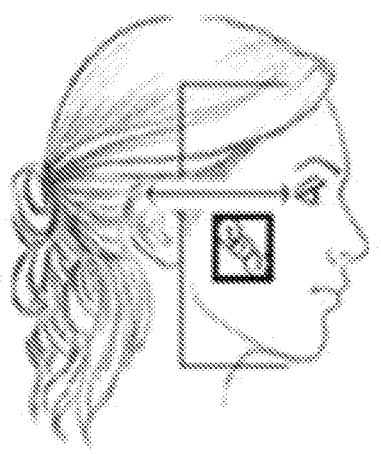

FIG. 3: Corneometer Measurement Areas

Figure 4:

FIG. 4: Eczema condition of a 6-year old female subject

Figure 5:

FIG. 5: Eczema condition of a 6-year old female subject 12 months after daily administration of herbal water supplement FIG. 6: Psoriasis condition on the back for a 52-year old male subject FIG. 7: Psoriasis condition on the back for a 52-year old male subject 12 months after daily administration of the herbal water supplement FIG. 8: Acne condition of a 18-year old female subject at start and after 6 months of daily administration of herbal water supplement FIG. 9: Nail health and Acanthosis nigricus improvement in a 18-year old female subject and after 6 months of daily administration of herbal water supplement

DETAILED DESCRIPTION

The following presents a detailed description of various embodiments of the present subject matter with reference to the accompanying drawings. The embodiments of the present subject matter are described in detail with reference to the accompanying drawings. However, the present subject matter is not limited to these embodiments which are only provided to explain more clearly the present subject matter to a person skilled in the art of the present disclosure.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements, and/or components, but do not preclude the presence or addition of one or more other features, steps, operations, elements, components, and/or groups thereof. As used herein, the term "and/or" includes any and all combinations of one or more of the described ingredients having similar properties.

The subject matter described herein relates to a method of improving functional and organoleptic properties of natural products and nutraceutical composition(s) thereof for the better skin care management.

The foregoing and further objects, features and advantages of the present subject matter will become apparent from the following description of exemplary embodiments with reference to the accompanying drawings.

It is to be noted, however, that the appended drawings illustrate only typical embodiments of the present subject matter, and are therefore, not to be considered for limiting of its scope, for the subject matter may admit to other equally effective embodiments.

Multi Herbal System Requirement

Most single herbs and spices to provide a particular functionality exhibit certain predominant mechanism of action. If we take skin care management, there are multiple processes that impact quality of skin care including skin elasticity, skin texture, skin hydration, pigmentation. These are complex processes that impact the skin tone and texture attributes known to those skilled in human physiology. A single herb or spice or plant may deliver one or more active ingredients that can impact a particular beneficial pathway. Due to diversity of physiology among humans, there could be one or more pathways that are deficient in the skin health pathway. By consuming one herb they may or may not effectively address the needs of a particular individual in skin care management. A multi-herbal system can address these short comings by simultaneously addressing various pathways and therefore the probability of a multi-herbal system to address the skin care management deficiencies increases significantly.

Consuming Many Herbs

While consuming multiple herbs would greatly help with addressing skin care management needs of many individuals, the challenges of developing and consuming multiple herbs daily poses several difficulties: 1. Identification of effective herbal formulation of multiple herbs; 2. Most of the herbs could only be effective when consumed or in topical applications in huge quantities lifelong which is humanly not possible; 3. The organoleptics of most natural materials are not suitable for daily consumption to deliver benefits continuously, 4. Achieving patient compliance remains a challenge with herbal formulations. The above are the most primary roadblocks towards development and administration of a multi-herbal formulations from the all the other issues known to a person skilled in the art.

Quantity of Herbs

The quantity of each of the herbs to deliver the required functionality is often large. Further, consuming large quantity of herbs and also herbs that have pungent tast'1q3w2e like ginger makes it very difficult to comply. This is due to low solubility of active ingredients in water. Most beneficial properties are delivered to a particular organ in a water-soluble form to deliver the needed benefit.

The multi-herbal system developed by the inventors of the present invention, with the active ingredients in a water-soluble form. All the benefits of multiple herbs in a water-soluble form have shown to deliver benefits to a much larger cross section of subjects.

Herbs & Spices Used in Current Invention

The object of the present invention is to provide a herbal composition comprising herbs from different families such as *Daucus carota, Amaranthus gangeticus* L, *Eclipta prostrata, Phyllanthus emblica, Curcuma longa, Piper longum, Psidium guajava, Ocimum basilicum, Salvia hispanica, Juglans regia, Linum usitatissimum, Prunus dulcis, Piper nigrum, Murraya koenigii, Glycyrrhiza glabra, Cinnamomum zeylanicum* Blume, *Cuminum cyminum, Trigonella foenum-graecum, Beta vulgaris, Punica granatum.*

*Daucus carota* Seeds or carrot seeds has several skin care benefits, together with the ability to rejuvenate dry and mature skin. "Carotol," a key component found in carrot seed oil is known to help firm and tone skin.

*Amaranthus gangeticus* L or Purple Amaranth are a storehouse of essential phytonutrients and antioxidants which help to reduce inflammation. The presence of an essential amino acids called lysine along with other elements are said to help fight against free radicals that result in wrinkles and signs of premature ageing, eczema and acne.

*Eclipta prostrata* or False Daisy is rich in anti-oxidants. Clinical studies indicate its benefits in skin care through lowering oxidative stress, including Ultraviolet (UV) irradiation-induced skin damage. False daisy extract contains an important flavonoid known as Luteolin. Luteolin penetrates the skin easily and reduces inflammation, promotes wound healing, and protects skin cells from damage caused by free radicals.

*Phyllanthus emblica*, commonly called as Indian Gooseberry or Amla helps protect the skin from the damaging effects of free radicals, non-radicals and transition metal-induced oxidative stress. *Phyllanthus emblica* is used in anti-aging, sunscreen and in general-purpose skin care products.

*Curcuma longa* or Turmeric is a commonly used spice throughout the world. It has been shown to exhibit anti-inflammatory, antimicrobial, antioxidant, and anti-neoplastic properties. Growing evidence shows that an active component of turmeric, curcumin, may be used medically to treat a variety of dermatologic conditions and diseases. Overall, there is evidence that turmeric/curcumin products and supplements, both oral and topical, may provide various therapeutic benefits for skin health.

*Piper longum* or Long Pepper which contains piperine and analogues or derivatives has shown re-pigmenting de-pigmented skin and for the treatment of skin. The piperine and analogues or derivatives are known to promote or enhance the natural coloration of the skin.

*Psidium guajava* leaves or Guava leaves extracts when applied on skin are known to loosen the dead skin cells, break the bonds between the dead skin cells and the base layer, thus helping to peel it from skin. When the dead skin layer is removed from skin, the skin becomes brighter, clear and free from any blemishes. Also, the high levels of anti-oxidants contained in *Psidium guajava* leaves provide diverse health and wellness benefits including reduction of oxidative stress in skin thereby providing anti-ageing benefits including wrinkle reduction.

*Ocimum basilicum* or Sweet Basil has been shown to provide various benefits in skin health including hydration, reduction in skin roughness, reduction in wrinkles. *Ocimum basilicum* provides an effective base to medicate topical acne-causing inflammation.

*Salvia hispanica* or Chia Seeds are a rich source of fatty acids, including omega-3 (as alpha-linoleic acid) plus unsaturated fatty acids linolenic and palmitic acids. They can help skin fight irritation, dehydration and in reducing blemishes.

*Juglans regia* or Walnut polyphenols, unsaturated fatty acids such as alpha linolenic acid and linoleic acid, essential amino acids, and minerals. The most abundant flavonoid in walnut is quercetin which exhibits anti-oxidant and anti-inflammatory activities. *Juglans regia* has skin protective effect by down-regulating the inflammatory response and anti-oxidant effects due to its polyphenolic compounds.

*Linum usitatissimum* or Flax Seed are packed with Omega-3 fatty acids, lignans and antioxidants. Omega-3 fatty acids help skin stay smooth and hydrated, while the lignans help reconstruct broken blood vessels and skin cells, and antioxidants protect the skin from free radicals and UV rays.

*Prunus dulcis* or Almonds are rich in anti-oxidants and vitamins which nourish skin and, keep it soft and supple. *Prunus dulcis* is also used as an exfoliator to get rid of impurities and to increase the smoothness of skin. Clinical studies have also shown that *Prunus dulcis* could prevent progression of normal ageing, including wrinkles through trans epidermal water loss and sebum production.

*Piper nigrum* or Black Pepper is used in natural skin care products for its analgesic, antiseptic, antispasmodic, anti-toxic, diaphoretic, diuretic, and rubefacient properties. Studies have also shown *Piper nigrum* protects skin from skin pigmentation and helps to maintain the original colour of skin.

*Murraya koenigii* or Curry Leaves are rich in anti-oxidants. They fight off free radicals in the skin and contribute in keeping the skin texture healthy and firm.

*Glycyrrhiza glabra* or Licorice contains Glabridin which helps maintain smooth, lighter tone and prevents the skin from darkening after sun exposure. And since sun damage is a primary cause of discoloration of the skin, Liquorice also contains UV blocking enzymes that help protect you from UV exposure damage.

*Cinnamomum zeylanicum* Blume or Cinnamon possesses anti-fungal, antioxidant and antibacterial properties and makes it useful against acne and skin blemishes. Cinnamon can also help remove acne by drying out the skin and by supporting blood flow to the skin.

*Cuminum cyminum* or Cumin is high in inflammation-fighting antioxidants to repair skin damage and keep skin looking young. Cumin is also naturally anti-bacterial, anti-microbial and anti-inflammatory to soothe skin and keep it blemish free. The essential oils contained in cumin help tone the skin and boost circulation.

The compounds in *Trigonella foenum-graecum* or Fenu-greek help with skin elasticity by tightening and firming up the skin. The vitamin C content in Fenugreek also enhances skin texture. Studies also indicate fenugreek helps with lowering blemishes and acne.

*Beta vulgaris* or Beetroot is rich in antioxidants such as beta carotene, vitamin C, and E, which aids in the regeneration of skin cells. Regular application of beet juice also helps to make the skin tone better by reducing blemishes, dark circles, and pigmentation of the skin.

*Punica granatum* or Pomegranate protect against premature aging by helping reduce the signs of skin aging caused by sun damage and exposure, such as wrinkles and fine lines. Pomegranates also help prevent hyperpigmentation and age spots.

Storage of Herbs & Spices, Grinding and Processes for Enhancing Organoleptic Properties of Herbs and Spices The storage of herbs and spices under controlled conditions of temperature & humidity, grinding of herbs and organoleptic processes enhancement via making slurry, filtration and distillation, ion exchange and carbon bed adsorption processes are discussed in detail in the Indian Patent application no: 202041041780 and the same is incorporated herewith by reference. The current invention uses the same steps discussed in this application. The formulation and the composition of the multiherb extract for current application in skin care management is accordingly modified. The processing conditions and ranges specified in the aforementioned patent application remain the same.

In the last three decades, a lot of concerted efforts have been channeled into researching into local plants with therapeutic values to address various health and wellness issues. The beneficial effects of some of these plants, herbs or spices have been validated and others disproved.

It is an object of the present invention to provide for a water based herbal formulation that addresses skin care management, skin related disorders and diseases among human subjects. The product formulation is prepared using the embodiments described in the Indian Patent application no: 202041041780 and the same is incorporated herewith by reference.

A herbal formulation for skin care management comprising extracts from *Daucus carota, Amaranthus gangeticus* L., *Eclipta prostrata, Phyllanthus emblica, Curcuma longa, Piper longum, Psidium guajava, Ocimum basilicum, Salvia hispanica, Juglans regia, Linum usitatissimum, Prunus dulcis, Piper nigrum, Murraya koenigii, Glycyrrhiza glabra, Cinnamomum zeylanicum* Blume, *Cuminum cyminum, Trigonella foenum-graecum, Beta vulgaris, Punica granatum.*

The aforesaid herbal formulation broadly comprises of the herbal constituents in the range of *Daucus carota* 0%-2.0%, *Amarantus Gangeticus* L 0-0.5%, *Eclipta prostrata* 0%-1.5%, *Phyllanthus emblica* 1.5%-10.5%, *Curcuma longa* 1.0%-11.0%, *Piper longum* 0.5%-6.5%, *Psidium guajava* 7.0%-30%, *Ocimum basilicum* 5.0%-28.0%, *Salvia hispanica* 0.5%-6.5%, *Juglans regia* 2.0%-27.5%, *Linum usitatissimum* 0.75%-6.5%, *Prunus dulcis* 1.75%-15.0%, *Piper nigrum* 1%-10%, *Murraya koenigii* 1.25%-7.5%,

*Glycyrrhiza glabra* 1.0%-11.0%, *Cinnamomum zeylanicum* Blume 2%-13.5%, *Cuminum cyminum* 0.25%-6.0%, *Trigonella foenum-graecum* 3.5%-22.0%, *Beta vulgaris* 0%-1.5%, *Punica granatum* 0%-2.85%.

The herbal formulation of the present invention could be manufactured using parts of the plants used for preparing the extracts are *Daucus carota* seeds, *Amaranthus gangeticus* L leaves, *Eclipta prostrata* leaves & stem, *Phyllanthus emblica* fruit, *Curcuma longa* root, *Piper longum* fruit, *Psidium guajava* leaves, *Ocimum basilicum* leaves, *Salvia hispanica* Seeds, *Juglans regia* Seed, *Linum usitatissimum* Seeds, *Prunus dulcis* Seeds, *Piper nigrum* flower, *Murraya koenigii* leaves, *Glycyrrhiza glabra* root, *Cinnamomum zeylanicum* Blume bark, *Cuminum cyminum* seeds, *Trigonella foenum-graecum* seeds, *Beta vulgaris* taproot, *Punica granatum* seeds & fruit.

As another embodiment the herbal formulation of the present invention comprises of the herbal constituents present in the ratio of *Daucus carota* 1.0%, *Amaranthus gangeticus* l 0.1%, *Eclipta prostrata* 0.70%, *Phyllanthus emblica* 6.0%, *Curcuma longa* 6.0%, *Piper longum* 2.4%, *Psidium guajava* 18.0%, *Ocimum basilicum* 17.7%, *Salvia hispanica* 3.6%, *Juglans regia* 6.0%, *Linum usitatissimum* 3.0%, *Prunus dulcis* 6.0%, *Piper nigrum* 4.0%, *Murraya koenigii* 2.8%, *Glycyrrhiza glabra* 5.8%, *Cinnamomum zeylanicum* Blume 5.5%, *Cuminum cyminum* 3.0%, *Trigonella foenum-graecum* 7.0%, *Beta vulgaris* 0.4%, *Punica granatum* 0.9%.

The embodiments of current invention have been shown to provide effective benefits to various aspect of skin health and wellness as described in following examples 1 to 5. They include overall improvement in skin conditions/properties including medical and/or cosmetic condition(s) like skin tone, texture, elasticity, hydration, spots, pigmentation, clarity, smoothness, open pores or pore size reduction, firmness, stretchmark reduction, Crow's feet, blackheads or whiteheads, pimples, oily skin, and possible scarring, acne, wrinkles, fine lines, Acanthosis nigricans (AN) or darkening of knuckles, Onychoschizia, splitting and chipping of nails and/or combination of the conditions. The formulation has demonstrated significant improvement in the treatment of autoimmune based conditions such as eczema, psoriasis and/or combination of the conditions or skin concerns for patients undergoing chemo therapy. Or skin ailments in general. A method of skin care management comprising administering to a subject an effective amount of herbal formulation as claimed in claim 1 for a time sufficient for skin revival.

As yet another embodiment, the present invention includes method of skin care management comprising administering to a subject an effective amount of herbal formulation as discussed in the examples for a time sufficient for skin revival.

Further, as yet another embodiment of the present invention, as described in the embodiments in international patent filing application, PCT/IN2021/051194, the formulation and accompanying embodiments of the application also show benefits relating to overall hair health including reduction in hair fall, improvements in hair density, hair follicle strength, hair density, hair tensile strength. Thus, a combination adjunctive therapy consisting of administering herbal waters in the current application along with herbal waters for hair care benefits as described in international patent filing application, PCT/IN2021/051194, could address both skin care and hair care issues encountered by patients undergoing chemo therapy. The two herbal water formulations may be administered together or sequentially—skin care herbal water administration followed by hair care herbal water administration or reverse sequence of administration.

The combination adjunctive therapy or sequential therapy is not just limited to conditions from chemo therapy, but can be applied to other conditions where skin and hair health are adversely effected.

EXAMPLES

The present invention is represented below by the help of representative examples. The examples do not limit the scope of the present invention.

Mixed Herbs Formulation

Herbs and spices were purchased and stored as per storage conditions specified in the Indian Patent application no: 202041041780. The following formulation summarized in Table 1 and covers the formulation used in the human clinical trial to demonstrate the benefits in terms of skin care management.

TABLE 1

| Ingredient Scientific Name | Weight % |
| --- | --- |
| *Daucus carota* | 1.00% |
| *Amaranthus gangeticus* L. | 0.10% |
| *Eclipta prostrata* | 0.70% |
| *Phyllanthus emblica* | 6.00% |
| *Curcuma longa* | 6.00% |
| *Piper longum* | 2.40% |
| *Psidium guajava* | 18.00% |
| *Ocimum basilicum* | 17.70% |
| *Salvia hispanica* | 3.60% |
| *Juglans regia* | 6.00% |
| *Linum usitatissimum* | 3.00% |
| *Prunus dulcis* | 6.00% |
| *Piper nigrum* | 4.00% |
| *Murraya koenigii* | 2.80% |
| *Glycyrrhiza glabra* | 5.90% |
| *Cinnamomum Zeylanicum Blume* | 5.50% |
| *Cuminum cyminum* | 3.00% |
| *Trigonella foenum-graecum* | 7.00% |
| *Beta vulgaris* | 0.40% |
| *Punica granatum* | 0.90% |
| Total | 100.00% |

Example 1

Mixed herbal powder Formulation summarized in Table 1 was used in the test. 14 kg of this mixed herbal powder was dispersed in 56 litres of water. The slurry was kept in suspension with a motorized impeller for 12 hours. The resultant slurry was charged to a 100 litre glass batch distillation still along condenser with a 2.5 sq m condensing surface area. The condenser was water cooled where water circulating at 3 deg C. inlet and 5 deg c outlet temperature. The glass vessel was immersed in a 50/50 ethylene glycol batch and heat input to the ethylene glycol was provided by an electrical heating element which was set at 150 deg C. The process was operated for 5 hours at a vacuum of 0.1 mm Hg (0.1 torr) and 30 litres of the herbal concentrate was collected. The boiling point of the batch was 41.6 degrees C. Overall process yield from herbal water to herbal condensate was 53.6%. The herbal condensate was crystal clear and free of any color.

Herbal extract produced was used as an adjunctive supplement in adjunctive nutraceutical therapy for skin care management as the ingredients used in the formulation are well known to be effective in skin care and specially to improve skin texture, tone, elasticity, hydration and pigmentation properties.

A single centric, open-label study to evaluate the efficacy of Skin Care Herbal Solution in the study participants was undertaken. Study was conducted for a period of 3 months for each subject and included a total of four (4) visits Visit 1 (Day 1) Screening visit & Baseline visit Visit 2 (Day 30)-assessment visit Visit 3 (Day 60)-assessment visit Visit 4 (Day 90)-assessment visit After obtaining informed consent, subjects who satisfied inclusion and exclusion criteria were enrolled. 40 subjects Instrument Assessments: Instrument Assessment to measure the elasticity, wrinkle & texture and skin hydration were performed using Cutometer, Antera and Corneometer respectively. Table 2 below shows the various instrument measurements performed during the clinical trial along with the frequency of measurements.

TABLE 2

| Instrument | Measurement site | Number of reading | Parameter | Assessment visits |
|---|---|---|---|---|
| Cutometer MPA580 | Cheek (Left and Right) | One independent reading | Elasticity | Baseline (day 1), day 30, day 60, day 90 |
| Antera 3D TM | Forehead (centre) and Crow's feet area - Right and left (same site for all assessment) | — | Wrinkle and texture | Baseline (day 1), day 30, day 60, day 90 |
| Corneometer | Forehead (centre) Cheek (Left and Right) | Three independent readings at different locations within the measurement area | Hydration | Baseline (day 1), day 30, day 60, day 90 | were enrolled in the study. A total of 39 subjects completed the study. Each subject was administered 15 ml of above mentioned herbal water mixed with 500 ml of water and consumed throughout the day.

A study-specific Informed Consent Form was signed by all subjects prior to screening. Sufficient time was provided to read and understand the information provided and ensuring that subjects were cognizant of the implications of enrolling in the study. The informed consent was obtained under ICH-GCP code of ethics. A written informed consent was taken from subjects willing to participate in the study. During the informed consent procedure, Clinical coordinators assisted the respective Dermatologists involved in the study.

The efficacy of the herbal water intervention was measured through three independent evaluations. They are:

1. Dermatological Assessments

2. Instrument Assessments

3. Subject Assessments

Dermatological Assessments: Dermatological assessment was done and recorded on dermatological assessment form on visits baseline (day 1), day 30, day 60, day 90. Parameters for assessment included:

In addition, detailed image analysis was performed using VISIA CR 2.2. Table 3 summarises the visual analysis procedures employed with the VISIA CR 2.2.

TABLE 3

| | |
|---|---|
| Visits on which the measurements are performed | Assessment visits: baseline (day 1), day 30, day 60, day 90 |
| Measurement side/view Number of images per side/view | Left, right and front view of the face CP (cross polarized) and PP (parallel polarized), S1(Standard 1) and S2(Standard 2) |

Data Analysis: The data of all 39 subjects who successfully completed the study was considered for the statistical analysis. Table 4 summarises the statistical analysis and criteria employed in the test. All statistical tests used significance level of $\alpha \leq 0.5$. Two tailed test was performed for all analysis. All p-values were rounded to 4 decimal places. All p-values that round to 0.000 was presented as '<0.0001' and p-values that round to 1.000 was be presented as '>0.9999'. Any p-value≤0.05 was considered statistically significant.

i.e.,

Suggestively significant for p-values 0.05<p<0.09

Statistically significant for p-value≤0.05

TABLE 4

| Statistics | Statistical test used | Description | Significance level |
|---|---|---|---|
| Normality Checking | Shapiro-Wilk Test | p-value from Shapiro-Wilk normality test at baseline | 5% |
| Efficacy Checking | Paired t-test/Wilcoxon signed rank test for paired samples | Mean Value comparison | 5% |

Skin Texture (9-point scale)

Skin firmness/Elasticity (9-point scale)

Crow's feet grading scale in unanimated face (photo numeric scale) to be evaluated using the left and right image profile (9-point scale)

Spots-Intensity (spot colour) and visibility (clarity) (9-point scale)

Evenness of skin tone (9-point scale)

Dermatological Assessment Data Analysis:

1. Skin Texture Score Basis: (0=none—best possible condition-Highly smooth, 1 to 3=Mild, 4 to 6=moderate, 7 to 9=severe (worst possible condition)—Very rough)

Table 5 sumamrises skin texture score & statistics by dermatologist during various points during the study

US 12,636,248 B2

15

TABLE 5

| N = 39 | Day 1 | Day 30 | Day 60 | Day 90 |
|---|---|---|---|---|
| Mean | 5.6 | 4.8 | 4.6 | 4.0 |
| St Dev | 1.1 | 1.1 | 1.1 | 0.8 |
| p Value (Baseline vs. Time Point) | | <0.001 | <0.001 | <0.001 |
| Difference vs Day 1 | | −14% | −18% | −28% |

Skin texture evaluation by the dermatologist indicated there was a significant improvement in skin texture observed at all time points posttest herbal water usage when compared to baseline. The improvement was seen as early as one month (Day 30) and was progressive with time.

2. Skin Firmness/Elasticity: An indirect visual/tactile assessment of skin elasticity determined by gently pulling the right and left cheeks skin lateral to the zygomatic arch and releasing it suddenly. Overall skin firmness is graded based on the rapidity with which the skin returns to its normal resting position. Grade 9 is assigned to skin that takes longer than 4 seconds to revert to normal position while Grade 0 is assigned to skin that returns to normal position instantaneously Firmness/Elasticity-Score 0—Very firm, 1 to 3—mild, 4 to 6=moderate, 7 to 9=Severe (Very loose)
Note: Lower mean value indicates improvement in skin firmness/elasticity Table 6 sumamrises skin firmness/elasticity & statistics by dermatologist during various points during the study.

TABLE 6

| N = 39 | Day 1 | Day 30 | Day 60 | Day 90 |
|---|---|---|---|---|
| Mean | 5.4 | 5.0 | 4.7 | 4.3 |
| St Dev | 0.9 | 0.9 | 1.0 | 0.8 |
| p Value (Baseline vs. Time Point) | | <0.001 | <0.001 | <0.001 |
| Difference vs Day 1 | | −7% | −14% | −22% |

There was a significant improvement in skin firmness observed at all time points post test herbal water usage when compared to baseline.

3. Crow's Feet grading scale in unanimated face: Crow's feet are wrinkles etched in the corner of the eye. Unlike wrinkles or expression lines on other areas of the face, crow's feet can appear to look deeper or more pronounced on the skin. Some of the leading causes of crow's feet include UV exposure and the loss of collagen and elasticity that come with age.
This was graded using a photonumeric scale of standards. Lower mean value indicates reduction in wrinkles.
Scale: 0=none (best possible condition), 1 to 3=mild, 4 to 6=moderate, 7 to 9=severe (worst possible condition)
Table 7 summarises mean Crows Feet grading scale for all clinical trial participants during the course of the clinical trial.

TABLE 7

| N = 39 | Day 1 | Day 30 | Day 60 | Day 90 |
|---|---|---|---|---|
| Mean | 3.5 | 3.5 | 3.5 | 3.3 |
| St Dev | 1.0 | 1.0 | 1.0 | 0.9 |
| p Value (Baseline vs. Time Point) | | NA | NA | 0.007 |
| Difference vs Day 1 | | 0% | 0% | −5% |

16

There was a significant improvement in wrinkles observed at day 90 post test herbal water usage when compared to baseline.

4. Spots Intensity (Colour)
Grading Scale: 0=none (Completely faded—best possible condition), 1 to 3=mild, 4 to 6=moderate, 7 to 9=severe (Very prominent—worst possible condition; Lower mean value indicates reduction in intensity of spots.
Table 8 summarises mean values of Spots intensity during the course of the clinical trial

TABLE 8

| N = 39 | Day 1 | Day 30 | Day 60 | Day 90 |
|---|---|---|---|---|
| Mean | 6.3 | 5.5 | 5.3 | 4.2 |
| St Dev | 0.8 | 1.0 | 0.9 | 1.5 |
| p Value (Baseline vs. Time Point) | | <0.001 | <0.001 | <0.001 |
| Difference vs Day 1 | | −12% | −15% | −33% |

There was a significant improvement in spot intensity observed at all time points post test herbal water usage when compared to baseline.

5. Skin Clarity
Grading Scale: 0=none (very clear—best possible condition), 1 to 3=mild, 4 to 6=moderate, 7 to 9=severe (Unclear—worst possible condition); Lower mean value indicates improvement in skin clarity.
Table 9 summarises mean values of Skin Clarity during the course of the clinical trial

TABLE 9

| N = 39 | Day 1 | Day 30 | Day 60 | Day 90 |
|---|---|---|---|---|
| Mean | 5.7 | 5.3 | 5.1 | 4.5 |
| St Dev | 1.3 | 1.2 | 1.2 | 1.1 |
| p Value (Baseline vs. Time Point) | | <0.001 | <0.001 | <0.001 |
| Difference vs Day 1 | | −7% | −10% | −21% |

There was a significant improvement in skin clarity observed at all time points post test herbal water usage when compared to baseline.

6. Evenness of Skin Tone
Grading Scale: 0=none (Even toned—best possible condition) 1 to 3=mild, 4 to 6=moderate, 7 to 9=severe (Highly uneven—worst possible condition); Lower mean value indicates improvement in skin tone.
Table 10 summarises mean values of Evenness of Skin Tone during the course of the clinical trial

TABLE 10

| N = 39 | Day 1 | Day 30 | Day 60 | Day 90 |
|---|---|---|---|---|
| Mean | 5.7 | 5.2 | 5.1 | 4.4 |
| St Dev | 1.2 | 1.1 | 1.0 | 1.1 |
| p Value (Baseline vs. Time Point) | | <0.001 | <0.001 | <0.001 |
| Difference vs Day 1 | | −8% | −10% | −22% |

There was a significant improvement in evenness of skin tone at all time points post test herbal water usage when compared to baseline.

Instrument Assessments:

1. Corneometer Assessment: The Corneometer indicates the hydration level of the superficial layers of the skin (stratum corneum) via measurement of skin dielectric properties. The measurements were performed by the applying the probe to the skin surface. Upon contact, an electric field passes through the stratum corneum and the dielectric constant is obtained. Increase in the value is a sign of improvement. Higher mean value indicates improvement Forehead Corneometer Assessment: Table 11 summarises mean corneometer measurements of hydration levels in forehead area during the course of the clinical trial

TABLE 11

| N = 39 | Day 1 | Day 30 | Day 60 | Day 90 |
|---|---|---|---|---|
| Mean | 42.5 | 46.0 | 50.2 | 55.0 |
| St Dev | 7.2 | 7.1 | 6.6 | 6.5 |
| p Value (Baseline vs. Time Point) | | <0.001 | <0.001 | <0.001 |
| Difference vs Day 1 | | 8% | 18% | 30% |

Cheek Corneometer Assessment: Table 12 summarises mean corneometer measurements of hydration levels in cheek area during the course of the clinical trial

TABLE 12

| N = 39 | Day 1 | Day 30 | Day 60 | Day 90 |
|---|---|---|---|---|
| Mean | 51.1 | 55.5 | 61.2 | 68.3 |
| St Dev | 6.4 | 6.8 | 6.0 | 6.5 |
| p Value (Baseline vs. Time Point) | | <0.001 | <0.001 | <0.001 |
| Difference vs Day 1 | | 9% | 20% | 34% |

There was a significant increase in mean values noted at all time points post test herbal water usage when compared to baseline in forehead and cheek areas implying significant improvement in skin hydration.

2. Cutometer Assessments: The Cutometer is intended to measure skin properties like elasticity and firmness of the skin. The principle is based on a mechanical deformation of the skin via the suction method. A negative pressure is created in the device and the skin is drawn into the 2 mm aperture of the probe. The resistance of the skin to the negative pressure (firmness) and its ability to return into its original position (elasticity) are displayed as real time measurement curves (penetration depth in mm/time). From these curves a variety of interesting measurement parameters can be calculated related to elastic and visco-elastic properties of skin surface and skin aging.

The typical shape of a curve of human skin is based on the different forces of elastin and collagen in the skin. Elastin is responsible for the Cutometer 4 curvesflexibility of the skin whereas collagen's main task is to keep the skin in shape.

The first, very straight part of the curve is shaped by the proportion of elastin in the skin as it easy to displace and very flexible. When skin starts to "creep" inside the probe, the collagen has taken over. It is stronger and resists the mechanical force better Immediately after the pressure of the device has ceased, the collagen starts to bring skin back to its original shape. Therefore, in young skin with fresh collagen, the skin instantly returns more closely to its original position than in aged skin. In the end, eventually the elastin sees to the complete recovery of the skin.

The software of the Cutometer® instrument allows to calculate a lot of interesting parameters from the different portions of the measurement curve. R-Parameters calculated by Cutometer are extremely well documented in literature for more than 20 years and briefly summarized below:

R0: stretchability/firmness mm (maximum amplitude of the curve)

R2: visco-elasticity in % (resistance to the mechanical force versus ability of returning)

R3: Tiring effect (Fatigue) visible for repeated suction/relaxation

R5: net elasticity: elastic portion of the suction part versus the elastic portion of the relaxation part %

R6: Portion of the visco-elasticity of the curve in %

R7: Portion of the elasticity compared to the complete curve in % a. R0 Values: Higher the values greater is the stretchability/firmness of the skin. Table 13 summarises the mean R0 values of the participants during the course of the clinical trial.

TABLE 13

| N = 39 | Day 1 | Day 30 | Day 60 | Day 90 |
|---|---|---|---|---|
| Mean | 0.29 | 0.35 | 0.38 | 0.42 |
| St Dev | 0.05 | 0.09 | 0.07 | 0.09 |
| p Value (Baseline vs. Time Point) | | <0.001 | <0.001 | <0.001 |
| Difference vs Day 1 | | 19% | 29% | 44% |

There was a significant increase in mean values noted at all time points post test herbal water usage when compared to baseline implying significant improvement in skin firmness.

b. R2 Values: Viscoelasticity or Gross elasticity, represents ability of re-deformation of the skin. The closer the value is to 1 (100%), the more elastic the skin. Table 14 summarises the mean R2 values of the participants during the course of the clinical trial.

TABLE 14

| N = 39 | Day 1 | Day 30 | Day 60 | Day 90 |
|---|---|---|---|---|
| Mean | 0.58 | 0.62 | 0.74 | 0.83 |
| St Dev | 0.10 | 0.13 | 0.10 | 0.08 |
| p Value (Baseline vs. Time Point) | | <0.001 | <0.001 | <0.001 |
| Difference vs Day 1 | | 6% | 27% | 43% |

There was a significant increase in mean values noted at all time points post test herbal waters usage when compared to baseline implying significant improvement in skin elasticity.

c. R3: Last curve, compared to the maximum amplitude of the first curve. "Tiring effects" of the skin are visible, as the amplitude increases with each new suction. Table 15 summarises the mean R3 values of the participants during the course of the clinical trial. In this parameter, higher the value, better the results.

TABLE 15

| N = 39 | Day 1 | Day 30 | Day 60 | Day 90 |
|---|---|---|---|---|
| Mean | 0.32 | 0.39 | 0.42 | 0.45 |
| St Dev | 0.05 | 0.09 | 0.07 | 0.10 |
| p Value (Baseline vs. Time Point) | | <0.001 | <0.001 | <0.001 |
| Difference vs Day 1 | | 21% | 29% | 39% |

There was a significant increase in mean values noted at all time points post test herbal water usage when compared to baseline implying significant improvement in skin elasticity.

d. R5: net elasticity: elastic portion of the suction part versus the elastic portion of the relaxation part %. Table 16 summarises the mean R5 values of the participants during the course of the clinical trial. In this parameter, higher the value, better the results.

TABLE 16

| N = 39 | Day 1 | Day 30 | Day 60 | Day 90 |
|---|---|---|---|---|
| Mean | 0.64 | 0.68 | 0.75 | 0.79 |
| St Dev | 0.13 | 0.13 | 0.12 | 0.10 |
| p Value Baseline vs. Time Point | | <0.001 | <0.001 | <0.001 |
| Difference vs Day 1 | | 6% | 17% | 23% |

There was a significant increase in mean values noted at all time points post test herbal water usage when compared to baseline implying significant improvement in skin elasticity.

e. R6: Portion of the visco-elasticity on the elastic part of the curve. Table 17 summarises the mean R6 values of the participants during the course of the clinical trial. In this parameter, the lower the value, better the results.

TABLE 17

| N = 39 | Day 1 | Day 30 | Day 60 | Day 90 |
|---|---|---|---|---|
| Mean | 0.65 | 0.53 | 0.45 | 0.33 |
| St Dev | 0.14 | 0.16 | 0.12 | 0.15 |
| p Value (Baseline vs. Time Point) | | <0.001 | <0.001 | <0.001 |
| Difference vs Day 1 | | −18% | −31% | −49% |

There was a significant decrease in mean values noted at all time points post test herbal water usage when compared to baseline implying significant improvement in skin elasticity.

f. Portion of elasticity compared to complete curve, closer to 1 (100%) the more elastic. Table 18 summarises the mean R7 values of the participants during the course of the clinical trial. In this parameter, higher the value, better the results.

TABLE 18

| N = 39 | Day 1 | Day 30 | Day 60 | Day 90 |
|---|---|---|---|---|
| Mean | 0.39 | 0.45 | 0.53 | 0.60 |
| St Dev | 0.08 | 0.10 | 0.10 | 0.11 |
| p Value (Baseline vs. Time Point) | | <0.001 | <0.001 | <0.001 |
| Difference vs Day 1 | | 16% | 35% | 54% |

There was a significant increase in mean values noted at all time points post test herbal water usage when compared to baseline implying significant improvement in skin elasticity.

3. Antera Assessments: ANTERA is an imaging-based software for skin assessment. All the measurements are performed on images captured using the Antera 3D camera at all times points. The software automatically generates a skin analysis report by comparing the images taken at different time points which includes fine lines, texture, pigmentation and wrinkles.

a. Antera—Wrinkles (Forehead). Table 19 summarises the mean values of wrinkles in the forehead area of participants during the course of the clinical trial. In this parameter, lower the value, better the results.

TABLE 19

| N = 39 | Day 1 | Day 30 | Day 60 | Day 90 |
|---|---|---|---|---|
| Mean | 23.9 | 20.3 | 19.0 | 17.9 |
| St Dev | 8.6 | 6.0 | 5.2 | 5.1 |
| p Value (Baseline vs. Time Point) | | <0.001 | <0.001 | <0.001 |
| Difference vs Day 1 | | −15% | −20% | −25% |

There was a significant decrease in mean values noted at all time points post test herbal water usage when compared to baseline implying significant improvement in wrinkles.

b. Antera—Texture (Forehead). Table 20 summarises the mean values of texture in the forehead area of participants during the course of the clinical trial. In this parameter, lower the value, better the results.

TABLE 20

| N = 39 | Day 1 | Day 30 | Day 60 | Day 90 |
|---|---|---|---|---|
| Mean | 20.7 | 17.6 | 16.4 | 15.6 |
| St Dev | 7.5 | 5.4 | 4.5 | 4.6 |
| p Value Baseline vs. Time Point | | <0.001 | <0.001 | <0.001 |
| Difference vs Day 1 | | −15% | −21% | −25% |

There was a significant decrease in mean values at time points post test herbal waters usage when compared to baseline implying significant improvement in skin texture.

c. Antera—Crow's Feet area (Wrinkles). Table 21 summarises the mean values of texture in the Crows Feet area of participants during the course of the clinical trial. In this parameter, lower the value, better the results.

TABLE 21

| N = 39 | Day 1 | Day 30 | Day 60 | Day 90 |
|---|---|---|---|---|
| Mean | 20.1 | 18.6 | 16.8 | 16.0 |
| St Dev | 8.3 | 7.8 | 6.8 | 6.8 |
| p Value (Baseline vs. Time Point) | | <0.001 | <0.001 | <0.001 |
| Difference vs Day 1 | | −7% | −16% | −20% |

There was a significant decrease in mean values noted at all time points post test herbal waters usage when compared to baseline implying significant reduction in wrinkles.

d. Antera—Crow's Feet area (Texture): Table 22 summarises the mean values of texture in the Crows Feet area of participants during the course of the clinical trial. In this parameter, lower the value, better the results.

TABLE 22

| N = 39 | Day 1 | Day 30 | Day 60 | Day 90 |
|---|---|---|---|---|
| Mean | 17.3 | 15.9 | 14.2 | 13.4 |
| St Dev | 7.5 | 6.9 | 6.1 | 5.8 |
| p Value (Baseline vs. Time Point) | | <0.001 | <0.001 | <0.001 |
| Difference vs Day 1 | | −8% | −18% | −23% |

There was a decrease in mean values at all time points post test herbal water usage when compared to baseline implying significant improvement in skin texture.

e. Antera—Spots: Table 23 summarises the mean values of spots which is the assessment of depigmentation of the skin of the participants during the course of the clinical trial. In this parameter, higher the value, better the results.

TABLE 23

| N = 39 | Day 1 | Day 30 | Day 60 | Day 90 |
|---|---|---|---|---|
| Mean | 41.2 | 42.2 | 43.3 | 43.7 |
| St Dev | 6.8 | 6.8 | 6.9 | 6.9 |
| p Value (Baseline vs. Time Point) | | <0.001 | <0.001 | <0.001 |
| Difference vs Day 1 | | 2% | 5% | 6% |

There was a significant increase in mean values at all time points post test herbal water usage when compared to baseline implying significant improvement in spot colour Subject Assessments:

Questionnaire: The following seven questions were asked to each subject during their visits to the organization administering the clinical trial. Subjects were asked to look at their face in mirror and score the attributes on Day 1, Day 30, Day 60 and Day 90

Scale:
    1: Strongly Disagree
    2: Disagree Somewhat
    3: Neither Agree nor Disagree
    4: Agree Somewhat
    5: Strongly Agree Questionnaire:
    1. Does your skin look firmer (tight)?
    2. Does your skin look younger?
    3. Does your skin look free of fine lines/wrinkles on your face (do not see small lines or folds observed near eye area, forehead etc.?
    4. Do you see reduction on age spots (pigments, dark spots) on your face?
    5. Is your skin moisturized?
    6. Does your skin look bright?
    7. Does your skin look even tone?

Results and Statistical Analysis of Questionnaire:
    1. Does your skin look firmer?
        Table 24 summarises the mean score of the subject questionnaire 1. Higher the value indicates firmer skin

TABLE 24

| N = 39 | Day 1 | Day 30 | Day 60 | Day 90 |
|---|---|---|---|---|
| Mean Score | 2.46 | 3.21 | 3.90 | 4.90 |
| St Dev | 0.60 | 0.41 | 0.31 | 0.31 |
| p Value (Baseline vs. Time Point) | | 0.0003 | <0.001 | <0.001 |
| Difference vs Day 1 | | 30% | 58% | 99% |

100% of the study population agreed that the skin looks firmer at Day-60 and Day-90.

2. Does your skin look younger?
        Table 25 summarises the mean score of the subject questionnaire 2. Higher the value indicates younger looking skin

TABLE 25

| N = 39 | Day 1 | Day 30 | Day 60 | Day 90 |
|---|---|---|---|---|
| Mean Score | 2.49 | 3.23 | 3.95 | 4.90 |
| St Dev | 0.60 | 0.43 | 0.22 | 0.31 |
| p Value (Baseline vs. Time Point) | | 0.0011 | <0.001 | <0.001 |
| Difference vs Day 1 | | 30% | 59% | 97% |

100% of the study population agreed that their skin looks younger at Day-60 and Day-90.

3. Does your skin look free of fine lines/wrinkles on your face (do not see small lines or folds observed near eye area, forehead etc.?
        Table 26 summarises the mean score of the subject questionnaire 3. Higher the value indicates lower fine lines/wrinkles

TABLE 26

| N = 39 | Day 1 | Day 30 | Day 60 | Day 90 |
|---|---|---|---|---|
| Mean Score | 2.46 | 3.36 | 4.00 | 4.67 |
| St Dev | 0.60 | 0.49 | 0.00 | 0.48 |
| p Value (Baseline vs. Time Point) | | 0.1081 | <0.001 | <0.001 |
| Difference vs Day 1 | | 36% | 63% | 90% |

100% of the study population agreed that the skin looks free of fine lines/wrinkles on face at Day-60 and Day 90.

4. Do you see reduction on age spots (pigments, dark spots) on your face?

Table 27 summarises the mean score of the subject questionnaire 4. Higher the value indicates lower age spots

TABLE 27

| N = 39 | Day 1 | Day 30 | Day 60 | Day 90 |
|---|---|---|---|---|
| Mean Score | 2.46 | 3.36 | 4.00 | 4.67 |
| St Dev | 0.60 | 0.49 | 0.00 | 0.48 |
| p Value (Baseline vs. Time Point) | | 0.1081 | <0.001 | <0.001 |
| Difference vs Day 1 | | 36% | 63% | 90% |

100% of the study population agreed that there was reduction in age spots on their face at Day-90.

5. Is your skin moisturized?

Table 28 summarises the mean score of the subject questionnaire 5. Higher the value indicates better skin moisturization.

TABLE 28

| N = 39 | Day 1 | Day 30 | Day 60 | Day 90 |
|---|---|---|---|---|
| Mean Score | 2.56 | 3.62 | 4.00 | 4.97 |
| St Dev | 0.55 | 0.49 | 0.00 | 0.16 |
| p Value (Baseline vs. Time Point) | | 0.1996 | <0.001 | <0.001 |
| Difference vs Day 1 | | 41% | 56% | 94% |

100% of the study population agreed that their skin looks moisturized at Day-60 and 90.

6. Does your skin look bright?

Table 29 summarises the mean score of the subject questionnaire 6. Higher the value indicates brighter skin.

TABLE 29

| N = 39 | Day 1 | Day 30 | Day 60 | Day 90 |
|---|---|---|---|---|
| Mean Score | 2.56 | 3.62 | 4.00 | 4.97 |
| St Dev | 0.55 | 0.49 | 0.00 | 0.16 |

TABLE 29-continued

| N = 39 | Day 1 | Day 30 | Day 60 | Day 90 |
|---|---|---|---|---|
| p Value (Baseline vs. Time Point) | | 0.1996 | <0.001 | <0.001 |
| Difference vs Day 1 | | 41% | 56% | 94% |

100% of the study population agreed that their skin looks bright at Day-60 and 90.

7. Does your skin look even tone?

Table 30 summarises the mean score of the subject questionnaire 7. Higher the value indicates more even tone skin.

TABLE 30

| N = 39 | Day 1 | Day 30 | Day 60 | Day 90 |
|---|---|---|---|---|
| Mean Score | 2.36 | 3.36 | 3.64 | 4.64 |
| St Dev | 0.71 | 0.54 | 0.54 | 0.49 |
| p Value (Baseline vs. Time Point) | | 0.0533 | 0.1996 | <0.001 |
| Difference vs Day 1 | | 42% | 54% | 97% |

100% of the study population agreed that the skin looks even toned at Day-90.

Table 31 summarises side by side comparison of dermatologist assessments, instrument assessments and subject assessments for similar set of parameters being assessed by a professional, by a scientific instrument with measured values and personal assessments by the individual clinical study participants. The data summarized in Table 31 below clearly shows the high degree of convergence in terms of each of the assessments. While quantitative values may be different from each assessment, the conclusions drawn are clearly consistent between various assessments. This clearly goes on to demonstrate the high degree of efficacy delivered by the embodiments of this invention.

TABLE 31

Dermatologist Assessment 1. Skin Texture Score (Observation with visual grading scales)

| | Day 1 | Day 30 | Day 60 | Day 90 |
|---|---|---|---|---|
| Mean | 5.6 | 4.8 | 4.6 | 4.0 |
| p Value | | <0.0001 | <0.0001 | <0.0001 |
| Difference vs Day 1 | 0.0% | -13.8% | -17.9% | -28.4% |

Lower value = Better Skin Texture

Instrument Measurements Anterra - Wrinkles & Texture 1. Forehead-Wrinkles (Instrument Measurement)

| | Day 1 | Day 30 | Day 60 | Day 90 |
|---|---|---|---|---|
| Mean | 23.9 | 20.3 | 19.0 | 17.9 |
| p Value | | <0.0001 | <0.0001 | <0.0001 |
| Difference vs Day 1 | | -14.9% | -20.4% | -25.2% |

Lower value = Lower Wrinkles

Instrument Measurements Anterra - Wrinkles & Texture 2. Forehead-Texture (Instrument Measurement)

| | Day 1 | Day 30 | Day 60 | Day 90 |
|---|---|---|---|---|
| Mean | 20.7 | 17.6 | 16.4 | 15.6 |
| p Value | | <0.0001 | <0.0001 | <0.0001 |
| Difference vs Day 1 | | -15% | -21% | -25% |

Lower value = Better Skin Texture

Self Assessment (Subjective Grading Scale)

| | |
|---|---|
| Mean | |
| p Value | |
| Difference vs Day 1 | |

Dermatologist Assessment 3. Crows Feet Grading (Observation with visual grading scales)

| | Day 1 | Day 30 | Day 60 | Day 90 |
|---|---|---|---|---|
| Mean | 3.5 | 3.5 | 3.5 | 3.3 |
| p Value | | NA | NA | 0.007 |
| Difference vs Day 1 | | 0.0% | 0.0% | -4.8% |

Lower value = Better Crows Feet Wrinkles

Anterra - Wrinkles & Texture 3. Crow's feet area-Wrinkles (Instrument Measurement)

| | Day 1 | Day 30 | Day 60 | Day 90 |
|---|---|---|---|---|
| Mean | 20.1 | 18.6 | 16.8 | 16.0 |
| p Value | | <0.0001 | <0.0001 | <0.0001 |
| Difference vs Day 1 | | -7.2% | -16.5% | -20.0% |

Lower value = Better Crows Feet Wrinkles

Anterra - Wrinkles & Texture 4. Crow's feet area-Texture (Instrument Measurement)

| | Day 1 | Day 30 | Day 60 | Day 90 |
|---|---|---|---|---|
| Mean | 17.3 | 15.9 | 14.2 | 13.4 |
| p Value | | <0.0001 | <0.0001 | <0.0001 |

TABLE 31-continued

| | Day 1 | Day 30 | Day 60 | Day 90 |
|---|---|---|---|---|
| Difference vs Day 1 | | -8.2% | -17.7% | -22.7% |

Lower value = Better Crows Feet Skin Texture

Dermatologist Assessment
2. Firmness/Elasticity-Score 0-Very firm, 1 to 3-mild, 4 to 6 = moderate, 7 to 9 = Severe (Very loose)

| | Day 1 | Day 30 | Day 60 | Day 90 |
|---|---|---|---|---|
| Mean | 5.4 | 5.0 | 4.7 | 4.3 |
| p Value | | <0.0001 | <0.0001 | <0.0001 |
| Difference vs Day 1 | | -7.3% | -13.7% | -21.7% |

Lower value = Better skin firmness & elasticity

Instrument Data Cutometer - Skin Elasticity Parameters
R0 - Passive Behavior of Skin to Force (Instrument Measurement)

| | Day 1 | Day 30 | Day 60 | Day 90 |
|---|---|---|---|---|
| Mean | 0.29 | 0.35 | 0.38 | 0.42 |
| p Value | | <0.0001 | <0.0001 | <0.0001 |
| Difference vs Day 1 | | 19.5% | 29.5% | 44.1% |

Higher value = Better results

Instrument Data Cutometer - Skin Elasticity Parameters
R2 - Gross Elasticity (Instrument Measurement)

| | Day 1 | Day 30 | Day 60 | Day 90 |
|---|---|---|---|---|
| Mean | 0.58 | 0.62 | 0.74 | 0.83 |
| p Value | | 0.0001 | <0.0001 | <0.0001 |
| Difference vs Day 1 | | 5.8% | 27.2% | 42.9% |

Higher the value = more elastic the skin

Instrument Data Cutometer - Skin Elasticity Parameters
R3 - Measures Tiring Effects of the Skin (Instrument Measurement)

| | Day 1 | Day 30 | Day 60 | Day 90 |
|---|---|---|---|---|
| Mean | 0.32 | 0.39 | 0.42 | 0.45 |
| p Value | | <0.0001 | <0.0001 | <0.0001 |
| Difference vs Day 1 | | 20.7% | 28.8% | 39.1% |

Higher the value = Better the snap back characteristics of the

Self Assessment (Subjective Grading Scale)
1. Does your skin look firmer (tight)?

| | Day 1 | Day 30 | Day 60 | Day 90 |
|---|---|---|---|---|
| Mean | 2.46 | 3.21 | 3.90 | 4.90 |
| p Value | | 0.0003 | <0.0001 | <0.0001 |

TABLE 31-continued

| | Day 30 | Day 60 | Day 90 |
|---|---|---|---|
| Difference vs Day 1 | 30.2% | 58.3% | 99.0% |

Self Assessment (Subjective Grading Scale)

3.Does your skin look free of fine lines/wrinkles on your face (do not see small lines or folds observed near eye area, forehead etc).?

| | Day 1 | Day 30 | Day 60 | Day 90 |
|---|---|---|---|---|
| Mean | 2.46 | 3.36 | 4.00 | 4.67 |
| p Value | | 0.1081 | <0.0001 | <0.0001 |
| Difference vs Day 1 | | 36.5% | 62.5% | 89.6% |

Cutometer - Skin Elasticity Parameters

R5 - Net Elasticity (Instrument Measurement)

| | Day 1 | Day 30 | Day 60 | Day 90 |
|---|---|---|---|---|
| Mean | 0.64 | 0.68 | 0.75 | 0.79 |
| p Value | | 0.0143 | <0.0001 | <0.0001 |
| Difference vs Day 1 | | 6% | 17% | 23% |

Higher the value = more elastic

R6 - Measures portion of the visco-elasticity on the elastic part of the curve (Instrument Measurement)

| | Day 1 | Day 30 | Day 60 | Day 90 |
|---|---|---|---|---|
| Mean | 0.65 | 0.53 | 0.45 | 0.33 |
| p Value | | 0.0010 | <0.0001 | <0.0001 |
| Difference vs Day 1 | | -17.9% | -30.9% | -48.6% |

Lower the value = higher the

Cutometer - Skin Elasticity Parameters

R7 - Measures Portion of the elasticity compared to the complete curve

| | Day 1 | Day 30 | Day 60 | Day 90 |
|---|---|---|---|---|
| Mean | 0.39 | 0.45 | 0.53 | 0.60 |
| p Value | | <0.0001 | <0.0001 | <0.0001 |
| Difference vs Day 1 | | 16% | 35% | 54% |

Higher the value = more elastic

Self Assessment (Subjective Grading Scale) 2. Does your skin look younger?

| | Day 1 | Day 30 | Day 60 | Day 90 |
|---|---|---|---|---|
| Mean | 2.49 | 3.23 | 3.95 | 4.90 |
| p Value | | 0.0011 | <0.0001 | <0.0001 |
| Difference vs Day 1 | | 29.9% | 58.8% | 96.9% |

TABLE 31-continued

Dermatologist Assessment 4. Spots Intensity

|  | Day 1 | Day 30 | Day 60 | Day 90 |
|---|---|---|---|---|
| Mean | 6.3 | 5.5 | 5.3 | 4.2 |
| p Value |  | <0.0001 | <0.0001 | <0.0001 |
| Difference vs Day 1 |  | -12.1% | -14.8% | -32.6% |

Lower Value meand lower spot intensity

**Instrument Data Anetera - Spots Spot-1 L* (Color Values)**

|  | Day 1 | Day 30 | Day 60 | Day 90 |
|---|---|---|---|---|
| Mean | 41.2 | 42.2 | 43.3 | 43.7 |
| p Value |  | <0.0001 | <0.0001 | <0.0001 |
| Difference vs Day 1 |  | 2.2% | 4.9% | 5.9% |

Higher mean value indicates improvement

**Self Assessment (Subjective Grading Scale)
4. Do you see reduction on age spots (pigments, dark spots) on your face?**

|  | Day 1 | Day 30 | Day 60 | Day 90 |
|---|---|---|---|---|
| Mean | 2.46 | 3.36 | 3.79 | 4.90 |
| p Value |  | 0.1081 | <0.0001 | <0.0001 |
| Difference vs Day 1 |  | 36.5 | 54.2 | 99.0 |

Higher mean value indicates improvement with respect to spots reduction

Dermatologist Assessment 5. Skin Visibility (Clarity)

|  | Day 1 | Day 30 | Day 60 | Day 90 |
|---|---|---|---|---|
| Mean | 5.7 | 5.3 | 5.1 | 4.5 |
| p Value |  | <0.0001 | <0.0001 | <0.0001 |
| Difference vs Day 1 |  | -6.8% | -9.7% | -21.4% |

Lower Value = Clearer Skin

Instrument Data Corneometer - Skin Hydration Forehead

|  | Day 1 | Day 30 | Day 60 | Day 90 |
|---|---|---|---|---|
| Mean | 42.5 | 46.0 | 50.2 | 55.0 |
| p Value |  | <0.0001 | <0.0001 | <0.0001 |
| Difference vs Day 1 |  | 8.5% | 18.2% | 29.6% |

Higher value = Better Skin Hydration

Instrument Data Corneometer - Skin Hydration Cheek

|  | Day 1 | Day 30 | Day 60 | Day 90 |
|---|---|---|---|---|
| Mean | 51.1 | 55.5 | 61.2 | 68.3 |
| p Value |  | <0.0001 | <0.0001 | <0.0001 |
| Difference vs Day 1 |  | 8.5% | 19.7% | 33.5% |

Higher value = Better Skin Hydration

TABLE 31-continued

Self Assessment (Subjective Grading Scale)
5. Is your skin moisturized?

|  | Day 1 | Day 30 | Day 60 | Day 90 |
|---|---|---|---|---|
| Mean | 2.56 | 3.62 | 4.00 | 4.97 |
| p Value |  | 0.1996 | <0.0001 | <0.0001 |
| Difference vs Day 1 |  | 41.0% | 56.0% | 94.0% |

Higher value = better skin moisturizer

Self Assessment (Subjective Grading Scale)
6. Does your skin look bright?

|  | Day 1 | Day 30 | Day 60 | Day 90 |
|---|---|---|---|---|
| Mean | 2.56 | 3.62 | 4.00 | 4.97 |
| p Value |  | 0.1996 | <0.0001 | <0.0001 |
| Difference vs Day 1 |  | 41.0% | 56.0% | 94.0% |

Higher value = brighter skin

Instrument Assessment

Dermatologist Assessment 6. Eveness of Skin tone

|  | Day 1 | Day 30 | Day 60 | Day 90 |
|---|---|---|---|---|
| Mean | 5.7 | 5.2 | 5.1 | 4.4 |
| p Value |  | <0.0001 | <0.0001 | <0.0001 |
| Difference vs Day 1 |  | -8.1% | -10.4% | -21.9% |

Lower Value = Better Skin Tone

Self Assessment (Subjective Grading Scale)
7. Does your skin look even tone?

|  | Day 1 | Day 30 | Day 60 | Day 90 |
|---|---|---|---|---|
| Mean | 2.36 | 3.36 | 3.64 | 4.64 |
| p Value |  | 0.0533 | 0.1996 | <0.0001 |
| Difference vs Day 1 |  | 42.4% | 54.3% | 96.7% |

Higher Value = Better Skin Tone

The Herbal solution described in example 2 was administered to a 6 year female subject suffering from acute Eczema. 15 ml of the herbal water was admixed in 500 ml of water and consumed in equal proportions at breakfast, lunch and dinner. FIG. 4 visually summarises the eczema condition on the hands which are clearly visible in the photograph. Twelve months after administering the herbal water, the patches on the skin were substantially absent as shown in FIG. 5.

The herbal water appears to effectively address eczema condition. The herbal nutraceuticals are addressing inflammation that could be arising from external factors such as allergens effectively.

Example 3

Figure 6:
Figure 7:
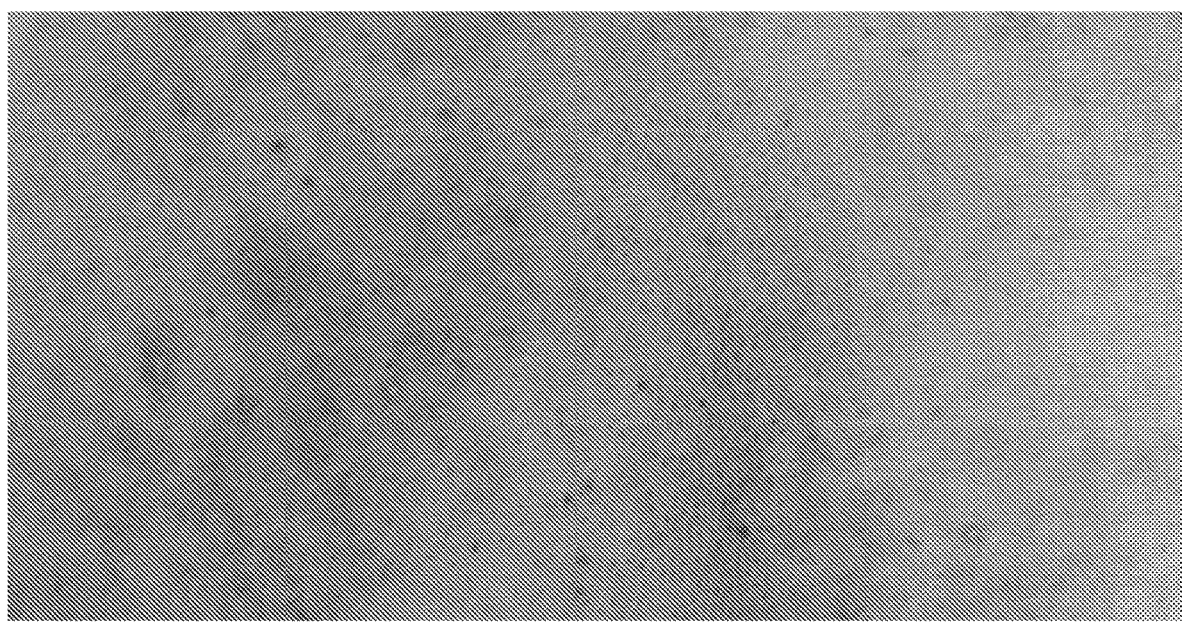

The Herbal solution described in example 2 was administered to a 52 year old male subject suffering from Psoriasis conditions in the back. 15 ml of the herbal water was admixed in 500 ml of water and consumed in equal proportions at breakfast, lunch and dinner. FIG. 6 visually summarises the psoriasis condition on the back. Twelve months after administering the herbal water, the psoriasis condition was greatly diminished as shown in FIG. 7.

The herbal water appears to effectively address immune system issues that are causative factors for psoriasis.

Example 4

Figure 8:

The Herbal solution described in example 2 was administered to a 18 year old female subject suffering from Acne. 15 ml of the herbal water was admixed in 500 ml of water and consumed in equal proportions at breakfast, lunch and dinner. FIG. 8 visually summarises the acne condition at start (photo on left hand side) and six months after consumption of herbal water (photo on right hand side).

The herbal water appears to effectively address acne by addressing the causative factors of Acne which may be a combination of anti-inflammatory and anti-bacterial properties.

Example 5

The solution described in example 2 was administered to a 18 year old female subject suffering from splitting and chipping of toe nail and also Acanthosis nigricans (AN) on the knuckles on the feet. 15 ml of the herbal water was admixed in 500 ml of water and consumed in equal proportions at breakfast, lunch and dinner.

Figure 9:

FIG. 9 visually summarises the nail and knuckles condition on the feet at start (photo on left hand side) and six months after consumption of herbal water (photo on right hand side).

The herbal water appears to effectively address acne by addressing the causative factors of nail health and it marked improvement in the nail appearance can be seen visually. Further, the dark pigmentation on the knuckles is shown to be reduced. The herbal water supplement appears to effectively address both nail condition or Onychoschizia and the dark pigmentation on knuckles or Acanthosis nigricans.

By combining multiple herbs into an easily consumable water format with good organoleptic properties in addition to good functional properties, it allows easy consumption of the herbal waters on a daily basis by subjects to achieve skin care management improvements.

The significant improvements on all aspects of skin care including skin elasticity, wrinkles, brightness, hydration, de-pigmentation has been uniquely addressed by consuming a nutraceutical rich water based herbal extract. The intervention appears to consistently deliver benefits as assessed by three independent sources—professional assessment by dermatologist, scientific instrument measurements and assessment and subject's personal assessment based on their own perception of the various skin attributes.

Although the invention has been described with reference to specific embodiments, this description is not meant to be construed in a limiting sense as it will become apparent to persons skilled in the art upon reference to the description of the invention. It is therefore, contemplated that such modifications can be made without departing from the spirit or scope of the present invention as defined.

The invention claimed is:

1. A herbal formulation for skin care management, skin related disorders and diseases comprising:

a composition derived as an aqueous extract or condensate of powdered plant parts in the following proportions by weight of the total formulation:

extracts from plant material comprising *Daucus carota* 0%-2.0%, *Amarantus gangeticus* L 0-0.5%, *Eclipta prostrata* 0%-1.5%, *Phyllanthus emblica* 1.5%-10.5%, *Curcuma longa* 1.0%-11.0%, *Piper longum* 0.5%-6.5%, *Psidium guajava* 7.0%-30%, *Ocimum basilicum* 5.0%-28.0%, *Salvia hispanica* 0.5%-6.5%, *Juglans regia* 2.0%-27.5%, *Linum usitatissimum* 0.75%-6.5%, *Prunus dulcis* 1.75%-15.0%, *Piper nigrum* 1%-10%, *Murraya koenigii* 1.25%-7.5%, *Glycyrrhiza glabra* 1.0%-11.0%, *Cinnamomum zeylanicum* Blume 2%-13.5%, *Cuminum cyminum* 0.25%-6.0%, *Trigonella foenum-graecum* 3.5%-22.0%, *Beta vulgaris* 0%-1.5%, and *Punica granatum* 0%-2.85% by weight of the herbal formulation.

2. The herbal formulation as claimed in claim 1, wherein the plant material comprises *Daucus carota* seeds, *Amaranthus gangeticus* L leaves, *Eclipta prostrata* leaves and stem, *Phyllanthus emblica* fruit, *Curcuma longa* root, *Piper longum* fruit, *Psidium guajava* leaves, *Ocimum basilicum* leaves, *Salvia hispanica* seeds, *Juglans regia* seeds, *Linum usitatissimum* seeds, *Prunus dulcis* seeds, *Piper nigrum* flower, *Murraya koenigii* leaves, *Glycyrrhiza glabra* root, *Cinnamomum zeylanicum* Blume bark, *Cuminum cyminum* seeds, *Trigonella foenum-graecum* seeds, *Beta vulgaris* taproot, and *Punica granatum* seeds and fruit.

3. The herbal formulation as claimed in claim 1, wherein the powdered plant parts are present in the following proportions by weight of the total formulation comprising:

| | |
|---|---|
| *Daucus carota* | 1.0%, |
| *Amaranthus Gangeticus* [[l]]L | 0.1%, |
| *Eclipta prostrata* | 0.70%, |
| *Phyllanthus emblica* | 6.0%, |
| *Curcuma longa* | 6.0%, |
| *Piper longum* | 2.4%, |
| *Psidium guajava* | 18.0%, |
| *Ocimum basilicum* | 17.7%, |
| *Salvia hispanica* | 3.6%, |
| *Juglans regia* | 6.0%, |
| *Linum usitatissimum* | 3.0%, |
| *Prunus dulcis* | 6.0%, |
| *Piper nigrum* | 4.0%, |
| *Murraya koenigii* | 2.8%, |
| *Glycyrrhiza glabra* | 5.8%, |
| *Cinnamomum Zeylanicum* Blume | 5.5%, |
| *Cuminum cyminum* | 3.0%, |
| *Trigonella foenum-graecum* | 7.0%, |
| *Beta vulgaris* | 0.4%, |
| *Punica granatum* | 0.9% | as weight percent of the herbal formulation.

as weight percent of the herbal formulation.

4. The herbal formulation as claimed in claim 1, wherein the herbal formulation is a herbal nutraceutical formulation.

5. A method of skin care management or nail treatment comprising:

administering to a subject an effective amount of herbal formulation as claimed in claim 1 for a time sufficient for treatment of the skin or nails.

6. The method of claim 5, wherein the skin treatment is selected from the group consisting of skin tone, skin texture, skin elasticity, skin hydration, spots on the skin, skin pigmentation, skin clarity, skin smoothness, open pores or pore size reduction, skin firmness, stretchmark reduction, reduction of crow's feet, blackheads or whiteheads, pimples, oily skin, scarring, acne, wrinkles, fine lines, acanthosis nigricans, and combinations thereof.

7. The method of claim 5, wherein the nail treatment is onychoschizia and/or chipping of the nails.

8. The method of claim 5, wherein the skin treatment is eczema and/or psoriasis.

9. The method of claim 5, wherein the skin treatment is for a skin ailment resulting from chemotherapy.

10. The method of claim 5, further comprising administering a hair care nutraceutical formulation adjunctively or sequentially to the subject for a time sufficient for treatment of the skin or nails and the hair.

\* \* \* \* \*